United States Patent [19]

Wideman

[11] 4,162,271
[45] Jul. 24, 1979

[54] SELECTIVE HYDROGENATION OF CYCLOPENTADIENE TO FORM CYCLOPENTENE USING RANEY NICKEL CATALYST AND ALCOHOLS BOILING ABOVE 95° C. IN THE REACTION MIXTURE

[75] Inventor: Lawson G. Wideman, Akron, Ohio

[73] Assignee: The Goodyear Tire & Rubber Company, Akron, Ohio

[21] Appl. No.: 850,576

[22] Filed: Nov. 11, 1977

[51] Int. Cl.² ............................................. C07C 5/02
[52] U.S. Cl. ..................................................... 585/274
[58] Field of Search ........................... 260/666 A, 667

[56] References Cited

U.S. PATENT DOCUMENTS

| | | | |
|---|---|---|---|
| 2,360,555 | 10/1944 | Evans et al. | 260/666 A |
| 3,022,359 | 2/1962 | Wiese et al. | 260/666 A |
| 3,937,745 | 2/1976 | Wideman et al. | 260/666 A |

*Primary Examiner*—Veronica O'Keefe
*Attorney, Agent, or Firm*—J. Y. Clowney

[57] ABSTRACT

There is disclosed a process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel in which an alcohol boiling above 99° C. is employed in the reaction mixture.

5 Claims, No Drawings

SELECTIVE HYDROGENATION OF CYCLOPENTADIENE TO FORM CYCLOPENTENE USING RANEY NICKEL CATALYST AND ALCOHOLS BOILING ABOVE 95° C. IN THE REACTION MIXTURE

BACKGROUND OF THE INVENTION

This invention is directed to a selective hydrogenation of dienes to monoolefins, particularly of cyclopentadiene to cyclopentene. More specifically, it is directed to a process whereby cyclopentadiene is selectively hydrogenated to cyclopentene through the use of a highly dispersed form of nickel in which alcohols which are liquid at the temperature of the hydrogenation, from about 0° to about 75° C., and which boil above 99° C., are used as the reaction medium. Such alcohols include: 1-heptanol, 2-heptanol, 3-heptanol, 4-heptanol, 1-methyl-1-hexanol, 2-methyl-1-hexanol, 3-methyl-1-hexanol, 1-methyl-2-hexanol, 2-methyl-2-hexanol, 3-methyl-2-hexanol, 2,3-dimethyl-1-pentanol, 1,3-dimethyl-1-pentanol, 1,3-dimethyl-2-pentanol, 1-hexanol, 2-hexanol, 3-hexanol, 2-methyl-1-pentanol, 2-methyl-3-pentanol, 3-methyl-1-pentanol, 3-methyl-2-pentanol, 3-methyl-3-pentanol, 2,3-dimethyl-1-butanol, 2-ethyl-1-butanol, 1-pentanol, 2-pentanol, 3-pentanol, 2-methyl-1-butanol, 3-methyl-1-butanol, 3-methyl-2-butanol, 2-methyl-2-butanol, 2-methyl-1-propanol, 2-butanol and 1-butanol, 1-octanol, 2-octanol, 4-methyl-1-heptanol, 5-methyl-1-heptanol, 5-methyl-2-heptanol, 3-methyl-3-heptanol, 5-methyl-3-heptanol, 2,4-dimethyl-1-pentanol, 2,3-dimethyl-3-pentanol, 4-methyl-1-pentanol, 4-methyl-2-pentanol, 2,2-dimethyl-1-butanol, and 3,3-dimethyl-1-butanol.

At the present time, substantial amounts of cyclopentadiene, usually as dicyclopentadiene, are available as a byproduct from the steam cracking of naphtha, which process produces primarily ethylene. Cyclopentene has been found to be useful as a monomer for the formation of general purpose elastomers by ring opening polymerization of cyclopentene. Therefore, it is desirable to convert a portion of the excess cyclopentadiene available into a more valuable raw material, such as cyclopentene.

The hydrogenation of cyclopentadiene to cyclopentene is not new. For instance, in U.S. Pat. No. 2,360,555, issued Oct. 17, 1944, there is disclosed a selective hydrogenation of one of the two conjugated double bonds of a cyclic diolefin to produce the corresponding cyclic monoolefin which is accomplished by conducting the hydrogenation in the liquid phase in the presence of an active hydrogenation catalyst, under moderate hydrogen pressure, such as 2 to 5 atmospheres absolute, and at relatively low temperatures, such as from 0° to 40° C. and even up to 100° C. using substantially less than the stoichiometric amount of hydrogen theoretically required to completely reduce the cyclic diene to the corresponding cyclic monoolefin. The catalyst therein disclosed is a pyrophoric nickel metal catalyst, such as Raney nickel. It is also disclosed that it is desired to conduct the reaction in dilute solution. The dilution may be affected by the addition of any solvent, stable under conditions of the process and which is not a catalyst poison and whose boiling point is such as to render it easily separable from the reaction mixture. Benzene and ethanol as well as tetralin, dioxane, isooctane, ethyl ether and diisopropyl ether are disclosed as such solvents in such process.

In U.S. Pat. No. 3,819,734, issued July 25, 1974, there is disclosed the hydrogenation of cyclopentadiene to cyclopentene by bringing cyclopentadiene into contact with a catalyst consisting essentially of (1) nickel, on a magnesium or zinc oxalate support, (2) a ligand selected from the group consisting of trimethyl phosphine, triethyl phosphine, methyl ethyl propyl phosphine, trimethyl phosphite, triethyl phosphite, tributyl phosphite, triphenyl phosphite, etc., while in the presence of hydrogen, at temperatures from 0° C. and at pressures from 0 to 1,000 pounds per square inch gauge. The solvent mentioned therein is ethanol.

In U.S. Pat. No. 3,994,986, issued Nov. 30, 1976, there is disclosed the preparation of cyclopentene from cyclopentadiene by hydrogenating cyclopentadiene with hydrogen gas at a ratio of 1 to 1.5 moles of hydrogen per mole of cyclopentadiene in the presence of a palladium catalyst on a carrier.

Also, in U.S. Pat. No. 3,857,894, issued Dec. 31, 1974, there is disclosed the hydrogenation of cyclopentadiene to cyclopentene in the presence of a palladium catalyst and an aqueous solution of zinc salt having a water/zinc ratio of at least 1/1 by weight.

The cyclopentadiene employed in the formation of cyclopentene by hydrogenation is usually obtained by depolymerizing or cracking dicyclopentadiene. In order to obtain cyclopentadiene for the hydrogenation of this invention, the depolymerization of dicyclopentadiene is accomplished by heating the dimer at a temperature above 150° C., under atmospheric pressure in a conventional cracking apparatus. The depolymerized material should be hydrogenated without substantial delay because it is also known that redimerization will occur upon standing.

SUMMARY OF THE INVENTION

According to the invention, cyclopentadiene is selectively hydrogenated to cyclopentene in a single liquid phase by contacting cyclopentadiene with hydrogen in the presence of a catalyst comprising a highly dispersed form of nickel and an alcohol selected from the group consisting of 1-heptanol, 2-heptanol, 3-heptanol, 4-heptanol, 1-methyl-1-hexanol, 2-methyl-1-hexanol, 3-methyl-1-hexanol, 1-methyl-2-hexanol, 2-methyl-2-hexanol, 3-methyl-2-hexanol, 2,3-dimethyl-1-pentanol, 1,3-dimethyl-1-pentanol, 1,3-dimethyl-2-pentanol, 1-hexanol, 2-hexanol, 3-hexanol, 2-methyl-1-pentanol, 2-methyl-3-pentanol, 3-methyl-1-pentanol, 3-methyl-2-pentanol, 3-methyl-3-pentanol, 2,3-dimethyl-1-butanol, 2-ethyl-1-butanol, 1-pentanol, 2-pentanol, 3-pentanol, 2-methyl-1-butanol, 3-methyl-1-butanol, 3-methyl-2-butanol, 2-methyl-2-butanol, 2-methyl-1-propanol, 2-butanol and 1-butanol, 1-octanol, 2-octanol, 4-methyl-1-heptanol, 5-methyl-1-heptanol, 5-methyl-2-heptanol, 3-methyl-3-heptanol, 5-methyl-3-heptanol, 2,4-dimethyl-1-pentanol, 2,3-dimethyl-3-pentanol, 4-methyl-1-pentanol, 4-methyl-2-pentanol, 2,2-dimethyl-1-butanol, and 3,3-dimethyl-1-butanol.

It has been found that in order to have a fairly selective hydrogenation of cyclopentadiene to cyclopentene, a reaction medium or diluent must be employed. Thus, according to the present invention, a high boiling alcohol, that is, one which will boil above 99° C. so that it will not azeotrope with cyclopentene is employed in the reaction mixture to act as a reaction medium or a diluent. As has been indicated, alcohols which boil below 99° C., when employed as a diluent in the hydrogenation of cyclopentadiene to cyclopentene, there is formed an azeotrope of cyclopentene with such alcohols, thus making it an added burden of separation of cyclopentene from the lower boiling alcohols such as ethyl, methyl and isopropyl alcohols.

The use of alcohols boiling above 99° C. as a reaction medium affords a single liquid phase hydrogenation system, both the cyclopentadiene and the cyclopentene being soluble therein. However, these alcohols boiling above 99° C. will not azeotrope with the cyclopentene thereby affording an ease of separation of the product cyclopentene from the reaction medium by means of simple distillation. These alcohols that boil above 99° C. also act as a heat sink thereby moderating the hydrogenation reaction resulting in high selectivity to cyclopentene.

DETAILED DESCRIPTION OF THE INVENTION

The temperature at which cyclopentadiene may be hydrogenated in accordance with this invention may range from 0° to 75° C. with 20° to 30° C. being most preferred. Temperatures that approach 100° C. tend to consume the cyclopentadiene in side reactions, such as dimerizations back to dicyclopentadiene and other undesirable side reactions. Generally speaking, both temperature and the pressure of hydrogen employed should be kept as low as possible consistent with reasonable rates of hydrogenation. When faster rates of reaction than that being obtained is desired, it is preferable to increase the rate of hydrogenation by means of increased hydrogen pressure rather than an increase in the temperature.

High hydrogen pressures may be employed to effect faster rates of hydrogenation, however, it has been found in accordance with the present invention that about 130 to about 150 psig/about 895.7 to about 1035.5 kPa, is all that is required to give a reasonable rate of reaction.

The catalyst employed in the present invention is a highly dispersed form of nickel. However, a Raney nickel-type catalyst is preferred. Methods for preparing the Raney nickel catalyst which are useful in this invention are known and can be found in a book entitled "CATALYTIC HYDROGENATION", by Robert L. Augstine, published in 1965 by Marcel Dekker, Inc., New York, N.Y.

Temperatures employed to prepare Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred, or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry, 14, 366, (1949). All of the Raney nickels described in the articles referred to above are operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez et al, the authors state that the T-1 Raney nickel is prepared as follows:

To a one-liter 3-neck flask containing 600 ml of a 10 percent sodium hydroxide solution, 40 grams of Raney nickel aluminum alloy (50 percent nickel) were added in small portions over a period of 20 to 30 minutes with mechanical stirring. The temperature was kept at 90°–95° C. during this addition. The mixture was stirred for an additional hour period at which time the stirring was stopped and the nickel was allowed to settle, and the solution decanted. The metal was washed five times with 200-ml portions of water and then five times with 50-ml portions of ethanol in such a manner that the nickel was always covered with liquid. The catalyst was then stored under ethanol and refrigerated for further use.

The Raney nickel employed in some of the examples of this invention, and termed by the present inventor as Modified T-1 Raney nickel, was prepared by a slight modification of Dominguez et al's procedure and is as follows:

A solution of two grams of sodium hydroxide in 50-ml of water was heated to its boiling point and then there was added two grams of Raney nickel aluminum alloy (one gram of Raney nickel) as rapidly as the hydrogen evolution would permit. This mixture was then digested at 95° to 100° C. for $\frac{1}{4}$ hour (reflux) and the water was continuatlly replaced as it evaporated. The solution was decanted from the Raney nickel and the metal washed with three 250-ml portions of cold water. This catalyst was employed without washing with ethanol.

The ratio of catalyst to cyclopentadiene is not too critical. It has been found satisfactory results are obtained when about one part by weight of catalyst per 500 parts by weight of cyclopentadiene are employed. When a catalyst to cyclopentadiene weight ratio greater than about one to 33 is employed, the catalyst is being wasted.

The amount of alcohol employed should range from about a volume ratio of alcohol to cyclopentadiene of about 1/1 to about 10/1. The actual volume ratio of alcohol to cyclopentadiene will depend upon the solubility of cyclopentadiene in the alcohol chosen and the hydrogenation rate desired.

The practice of this invention is further illustrated by reference to the following examples which are intended to be representative rather than restrictive of the scope of the invention. Unless otherwise indicated, all parts and percentages are by weight.

EXAMPLE 1

In a one-liter stainless-steel reactor which had been swept with nitrogen, there was charged one gram (g) of modified T-1 Raney catalyst (MODT-1) in about 10 milliliters (ml) of water, followed by 200-ml of alcohol, as set forth in column 2 of the table below. Then, 66 g of cyclopentadiene containing 5.0 g of pentane as a chromatographic internal standard was charged to the reactor. The reactor was then sealed and charged with hydrogen and maintained between the range as set forth in the table below. The temperature of the reaction was held at 25° C. by means of internal cooling coils and the reaction was stopped when about 95 percent of the theoretical amount of hydrogen had been consumed. The stirring was discontinued and the hydrogen pressure vented to about one atmosphere. The alcoholic solution of cyclopentene and unreacted cyclopentadiene was decanted from the catalyst and subjected to gas chromatographic analysis. The results and operating conditions are set forth in the table below. In Run #6, only one-half gram of modified T-1 catalyst was employed.

Table 1

| Run No | Catalyst (g) | Solvent (ml) | Rxn Time (min) | H₂ Pres (psig) | Conv CPD (%) | Sel CPE (%) | Sel CPA (%) |
|---|---|---|---|---|---|---|---|
| 1 | 1.0g Mod T-1 | S-butanol | 25 | 125-150 | 93.4 | 99.0 | 0.3 |
| 2 | 1.0g Mod T-1 | iso-butanol | 20 | 100-150 | 94.0 | 99.0 | 0.4 |
| 3 | 1.0g Mod T-1 | s-butanol | 20 | 100-150 | 93.4 | 99.5 | 0.3 |
| 4 | 1.0g Mod T-1 | n-butanol | 26 | 100-150 | 96.1 | 99.5 | 0.5 |
| 5 | 1.0g Mod T-1 | s-butanol | 34 | 50-100 | 95.6 | 99.4 | 0.6 |
| 6 | 0.5g Mod T-1 | s-butanol | 80 | 100-150 | 92.6 | 98.4 | 1.6 |

While certain representative embodiments and details have been shown for the purpose of illustrating the invention, it will be apparent to those skilled in this art that various changes and modifications may be made therein without departing from the spirit or scope of the invention.

What is claimed is:

1. In a process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel selected from the group comprising Raney nickel or a modified Raney nickel the improvement comprising using an alcohol boiling above 99° C. as the reaction medium and in which the volume ratio of alcohol to cyclopentadiene ranges from 1/1 to 10/1.

2. The process according to claim 1 in which the alcohol is selected from the group consisting of 1-heptanol, 2-heptanol, 3-heptanol, 4-heptanol, 1-methyl-1hexanol, 2-methyl-1-hexanol, 3-methyl-1-hexanol, 1-methyl-2-hexanol, 2-methyl-2-hexanol, 3-methyl-2-hexanol, 2,3-dimethyl-1-pentanol, 1,3-dimethyl-1-pentanol, 1,3-dimethyl-2-pentanol, 1-hexanol, 2-hexanol, 3-hexanol, 2-methyl-1-pentanol, 2-methyl-3-pentanol, 3-methyl-1-pentanol, 3-methyl-2-pentanol, 3-methyl-3-pentanol, 2,3-dimethyl-1-butanol, 2-ethyl-1-butanol, 1-pentanol, 2-pentanol, 3-pentanol, 2-methyl-1-butanol, 3-methyl-1-butanol, 3-methyl-2-butanol, 2-methyl-2-butanol, 2-methyl-1-propanol, 2-butanol and 1-butanol, 1-octanol, 2-octanol, 4-methyl-1-heptanol, 5-methyl-1-heptanol, 5-methyl-2-heptanol, 3-methyl-3-heptanol, 5-methyl-3-heptanol, 2,4-dimethyl-1-pentanol, 2,3-dimethyl-3-pentanol, 4-methyl-1-pentanol, 4-methyl-2-pentanol, 2,2-dimethyl-1-butanol and 3,3-dimethyl-1-butanol.

3. The process according to claim 2 in which the temperature ranges from 20° to 30° C.

4. The process according to claim 2 in which the pressure of the hydrogen is about 150 psig -- 1035.5kPa.

5. The process according to claim 2 in which the alcohol is selected from the group consisting of 1-butanol or 2-butanol.

* * * * *